(12) United States Patent
Sanduja et al.

(10) Patent No.: US 6,180,039 B1
(45) Date of Patent: *Jan. 30, 2001

(54) GERMICIDALLY PROTECTED CONVEYOR COMPONENTS AND METHODS FOR THEIR PRODUCTION

(75) Inventors: Mohan L. Sanduja, Flushing; Carl Horowitz, Brooklyn; Mohammed Kamruzzaman, Bronx; Paul Thottathil, New Hyde Park, all of NY (US); Earl A. Ramsey, Sinking Springs, PA (US)

(73) Assignee: Rainbow Industrial Products Corp., Denver, PA (US)

( * ) Notice: Under 35 U.S.C. 154(b), the term of this patent shall be extended for 0 days.

This patent is subject to a terminal disclaimer.

(21) Appl. No.: 09/362,986

(22) Filed: Jul. 30, 1999

Related U.S. Application Data

(62) Division of application No. 08/835,931, filed on Apr. 11, 1997, now Pat. No. 6,039,964.

(51) Int. Cl.⁷ .......................... B29C 47/00; B29C 45/00; B29C 43/00
(52) U.S. Cl. .................. 264/211; 264/320; 264/331.11; 264/328.1; 198/850
(58) Field of Search .................................. 264/211, 349, 264/320, 328.1, 331.11; 424/405; 198/850–853

(56) References Cited

U.S. PATENT DOCUMENTS

| | | |
|---|---|---|
| 3,782,398 | 1/1974 | Powell et al. . |
| 3,885,525 | 5/1975 | Powell et al. . |
| 3,924,381 | 12/1975 | Sardo . |
| 4,086,297 | 4/1978 | Rei et al. . |
| 4,401,770 | 8/1983 | Hance . |
| 4,533,435 | 8/1985 | Intili . |
| 4,617,328 | 10/1986 | Liu . |
| 4,666,956 | 5/1987 | Spielau et al. . |
| 4,935,232 | 6/1990 | McIntosh . |
| 4,937,273 | 6/1990 | Okuyama et al. . |
| 4,989,723 | 2/1991 | Bode et al. . |
| 4,996,052 | 2/1991 | McIntosh . |
| 5,069,907 | 12/1991 | Mixon et al. . |
| 5,083,659 | 1/1992 | Bode et al. . |
| 5,194,454 | 3/1993 | Chatelin et al. . |
| 5,232,748 | 8/1993 | Horowitz et al. . |
| 5,238,749 | 8/1993 | Cueman et al. . |
| 5,342,659 | 8/1994 | Horowitz et al. . |
| 5,441,742 | 8/1995 | Autant et al. . |
| 5,482,989 | 1/1996 | Koskinieme . |
| 5,495,935 | 3/1996 | Zabron et al. . |
| 5,586,643 | 12/1996 | Zabron et al. . |
| 5,613,597 | 3/1997 | Palmaer et al. . |
| 5,614,568 | 3/1997 | Mawatari et al. . |
| 5,789,461 * | 8/1998 | Nicolson et al. ............. 523/106 |
| 6,039,964 * | 3/1999 | Sanduja et al. ............... 424/404 |

\* cited by examiner

*Primary Examiner*—Jan H. Silbaugh
*Assistant Examiner*—Mark Eashoo
(74) *Attorney, Agent, or Firm*—Nixon & Vanderhye

(57) ABSTRACT

Process for fabricating a conveyor component having germicidal properties, in which a blend of a polymeric material and a composition comprising a polymerizable monomer and a germicidal agent is molded to form a conveyor component having germicidal properties comprising a solid unitary polymeric material and a polymerized salt of a polymerizable monomer and a germicidal agent grafted to the polymeric material and distributed uniformly throughout the polymeric material.

5 Claims, 3 Drawing Sheets

GERMICIDALLY PROTECTED CONVEYOR COMPONENTS AND METHODS FOR THEIR PRODUCTION

This is a divisional of application Ser. No. 08/835,931 filed Apr. 11, 1997, now U.S. Pat. No. 6,039,964.

The present invention relates generally to the treatment of polymeric materials to impart germicidal properties thereto. More particularly, the present invention provides compositions and methods for treating polymeric materials used in the fabrication of conveyor components employed in the food handling industry in order to impart germicidal properties thereto.

BACKGROUND OF THE INVENTION

It is well known to employ conveyor systems in food processing environments. The surfaces of these conveyor systems are subject to contamination by various types of microbes and bacteria which gives rise to a health hazard in the transportation of food. This can result in the food having to be destroyed and well as other health problems which, in turn, gives rise to increased costs of operation. A need exists, therefore, for a way of protecting conveyor systems and conveyor components used in the food handling industry from bacterial and microbial growth to thereby provide safe and hygienic surfaces. The present invention seeks to meet that need.

SUMMARY OF THE INVENTION

According to one aspect of the present invention, there is provided a composition suitable for use in the fabrication of conveyor components in order to impart germicidal properties thereto, comprising a polymerized salt of a polymerizable monomer and a germicidal agent.

In accordance with another aspect of the invention, there is provided a conveyor component having germicidal properties comprising a solid unitary polymeric material and a polymerized salt of a polymerizable monomer and a germicidal agent distributed uniformly throughout the body of the polymeric material.

In accordance with a yet further aspect of the invention, there is provided a process for fabricating a solid unitary conveyor component having germicidal properties, in which a blend of a polymeric material and a composition comprising a polymerizable monomer and a germicidal agent is molded to form the solid unitary component with the germicidal agent distributed uniformly throughout the body of the component.

Use of the compositions of the invention in the molding of conveyor components results in chemcial grafting of the germicidal agent to the polymer material to bond the germicidal agent thereto. As a result, the germicidal agent does not migrate out of the polymeric material, and the useful life of the germicidally protected conveyor components of the invention is thereby extended.

BRIEF DESCRIPTION OF THE DRAWINGS

The invention will be described in more detail with reference to the accompanying drawings, in which.

DETAILED DESCRIPTION OF PREFERRED EMBODIMENTS

Figure 1:
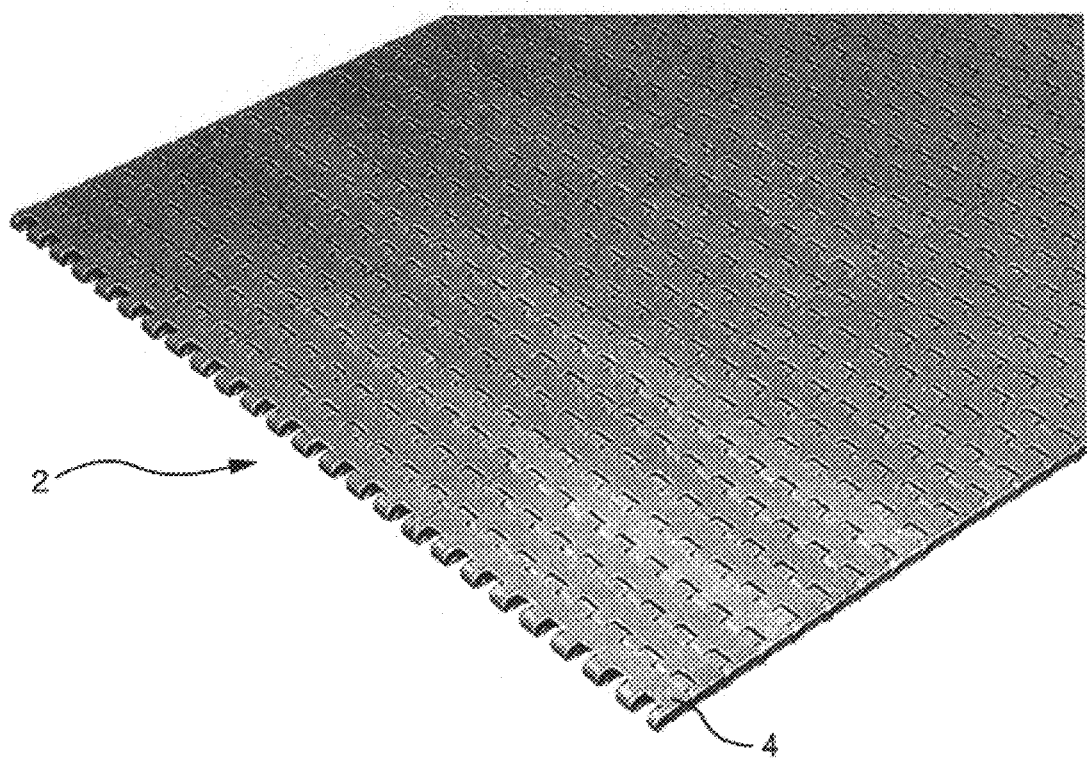
FIG. 1 shows a conveyor component of the invention in the form of a conveyor belt.

The term "conveyor component" as used herein includes any component of a conveyor system which comes into contact or is likely to come into contact with food during operation of the conveyor system. The term includes items such as conveyor belts, chains, and drive components for belts and chains, including sprockets, pulleys and wearstrips, fabricated from sheets and profiles, which may be machined or extruded from polymeric material(s).

The term "germicidal agent" as used herein includes any compound having bacteriostatic, fungicidal and/or antimicrobial activity. The term includes any compound having the ability to inhibit and/or control the growth of microorganisms, including but not limited to bacteria, fungi and yeasts. Examples of species against which germicidal action is achieved according to the present invention are *Escherichia coli, Salmonella choleraesuis*, Staphylococcus, Aspergillus, Streptococcus, Klebsiella, Listeria and Clostridium.

The term "polymeric material" as used herein includes any suitable polymeric material used in the fabrication of conveyor components. Examples of typical polymeric materials are polypropylene, polyethylene, nylon, acetal and polyurethane.

The term "polymerizable monomer" includes any suitable monomer or prepolymer, such as vinylidine chloride, chloroprene, isoprene, dimethylaminomethyl acrylate, styrene, 1,3-butylene dimethacrylate, hydroxyethyl methacrylate, isoctylvinyl ether, acrylonitrile, acrylamide, N-vinyl pyridine, glycidyl methacrylate, N-vinyl caprolactam, N-vinyl pyrrolidone, N-vinyl carbazole, acrylic acid, methacrylic acid, ethyl acrylate, ethyl methacrylate, itaconic acid, isobutyl methacrylate, methyl acrylate, sodium styrene sulfonate, sodium vinyl sulfonate, bis (beta-chloroethyl) vinyl phosphate, cetyl vinyl ether, divinyl ether of ethylene glycol, divinyl ether of butane diol, vinyl toluene, vinyl acetate and octadecyl vinylether. Amines can be quaternized with benzyl chloride, ethyl iodide, methyl or ethyl sulfate. Monomeric chlorides can be quaternized with tertiary amines to give quaternary ammonium compounds. Examples of tertiary amines are n-ethyl morpholine, pyridine, cetyldimethyl pyridine and methyl methacrylate.

Preferred polymerizable monomers are anionic monomers which contain either sulfonic (—$SO_3H$) or carboxyl (—COOH) groups and are preferably those of the vinyl or acrylic type. Suitable anionic polmerizable monomers are ethyleneimine, hydroxyethyl methacrylate, dimethylaminoethyl methacrylate, ethylacrylate, butylacrylate, as well as carboxylated and sulfonated vinyl compounds such as vinyl chloride, vinyl pyrrolidine, vinylidene, chloride and vinylidene bromide.

The germicidal agent is typically a cationic germicidal agent. Examples of suitable cationic germicidal agents which may be used are zinc omadine, cetyl pyridinium chloride and Barquat 4250. These may be used alone or in combination with each other. Zinc omadine is particularly preferred. This compound exhibits both bactericidal and fungicidal activity and is a highly active broad spectrum antimicrobial compound. The compound is used in personal care applications, and is registered with the Environmental Protection Agency for a variety of industrial uses. Zinc omadine is a derivative of pyrithione and is listed in the Chemical Abstracts Registry as zinc pyrithione: bis [1-hydroxy-2(1H)-pyridinethionato-O.S]-(T-4) zinc (CAS No.: (13463-41-7).

While not bound by any particular theory, it is believed that attachment of the cationic germicidal agent to the polymeric material takes place by way of salt formation between the cationic germicidal agent and the anionic polymerizable monomer which is in turn grafted to the polymeric material throughout the mass of the polymeric material, via a free radical mechanism. The reaction steps believed to be involved are set forth below.

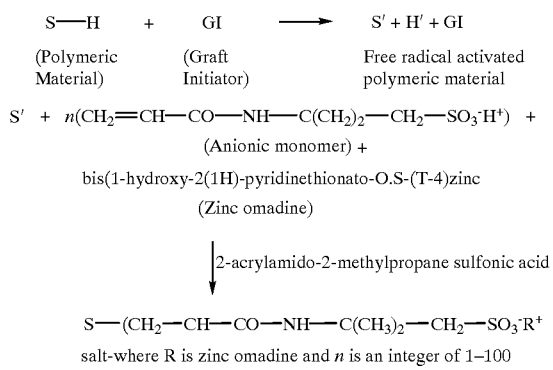

The composition of the invention comprises in its broadest aspect an effective amount of a germicidal agent and a polymerizable monomer. By "effective amount of germicidal agent" is meant an amount sufficient to obtain a desired antimicrobial and/or antibacterial effect when the germicidal agent is incorporated into the molded conveyor component. The concentration of the germicidal agent in the solution can vary within any desired range, and is usually from about 0.5% to 90% by weight of the solution. The amount of polymerizable monomer in the solution is generally about 0.05% to 10% by weight of the solution, and is generally present in an amount which is about one tenth of the amount of the germicidal agent. However, the germicidal agent may if desired be used in an approximately 1:1 mole ratio with respect to the polymerizable monomer.

Generally, it is desired that the germicidal agent be present in the final molded conveyor component in an amount of 0.5 to 15% by weight of the component. More usually, this amount is about 1% to 10% by weight, typically 5–10% by weight.

The compositions of the invention may also comprise a catalyst and a graft initiator system. Examples of suitable catalysts which may be employed are ammonium persulfate, hydrogen peroxide, tert-butyl hydroperoxide, ditert-butyl peroxide, benzoyl peroxide, dicumyl peroxide, lauroyl peroxide, tert-butyl perbenzoate and peracetic acid. The catalyst is present in a catalytically effective amount sufficient to achieve the desired catalytic effect. The determination of this effective amount is well within the skill the worker in this field.

Examples of suitable graft initiators are ferrous or ferric ions, silver oxide or particles of silver. The metal particles or ions may be formed in situ during the molding operation to form the conveyor component. The silver may be introduced by way of aqueous silver nitrate solution. The ferrous ions may be introduced by way of aqueous ferrous ammonium sulfate solution. The concentration of the silver or ferrous solution can vary widely, but is generally within about 0.5% to 5% by weight.

Examples of suitable solvents which may be used are dimethylformamide, tetrahydrofuran, tetrahydrofuryl alcohol, dimethyl sulfoxide, water, methyl ethyl or isopropyl alcohol, acetone, methyl ethyl ketone and ethyl acetate. Mixtures of the above solvents may also be used.

The compositions of the invention are typically prepared by admixing or blending at room temperature the cationic germicidal agent, the anionic polymerizable monomer, catalyst and graft initiator, optionally in the presence of a solvent. Typically, this mixing is carried out by placing the germicidal agent in a container, adding the monomer, catalyst and graft initiator and solvent if used to the container and stirring to obtain a uniform mix.

The resulting composition is then added to the polymeric material (which may be polypropylene, polyethylene, Nylon, Delrin (Acetal) or polyurethane) and the contents stirred at room temperature to provide a uniform mix. The resulting blend is then molded by injection, extrusion and/or compression molding to graft the germicidal agent onto the polymeric material to form the desired germicidally protected conveyor component. The molding is carried out at elevated temperature employing conventional techniques and conditions. Typically the molding is performed in the range of about 175 to 250° F., depending on the melting point of the polymer. It is during this high temperature molding that the grafting reaction occurs to cause the germicidal agent to become attached to the polymeric material. The molding is otherwise carried out under conditions and using apparatus which are conventional in the art.

Figure 2:
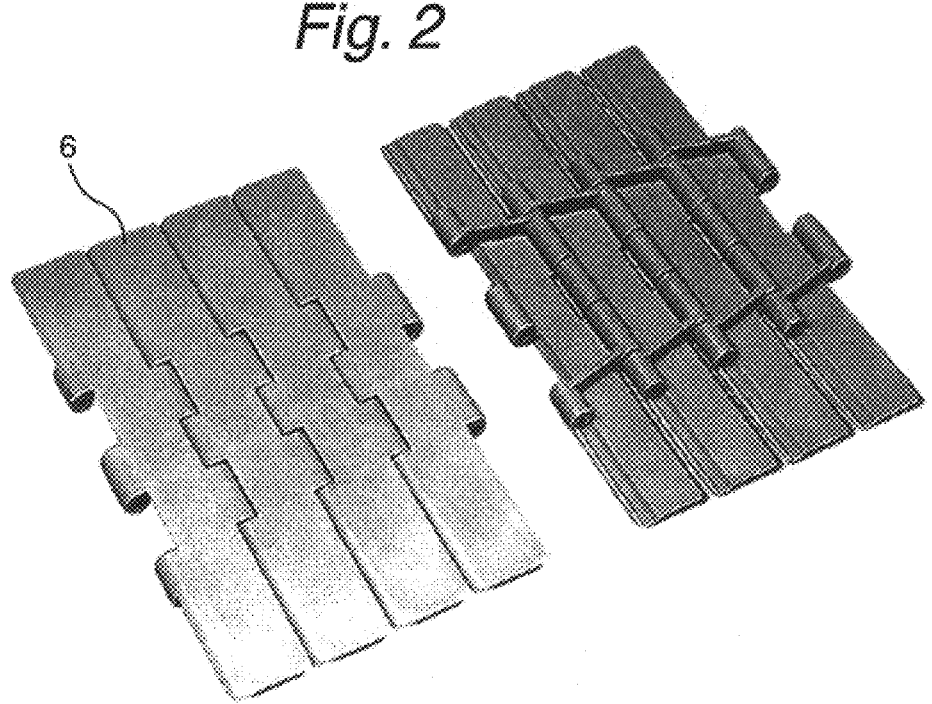
FIG. 2 shows a conveyor component of the invention including a running chain.
Figure 3:
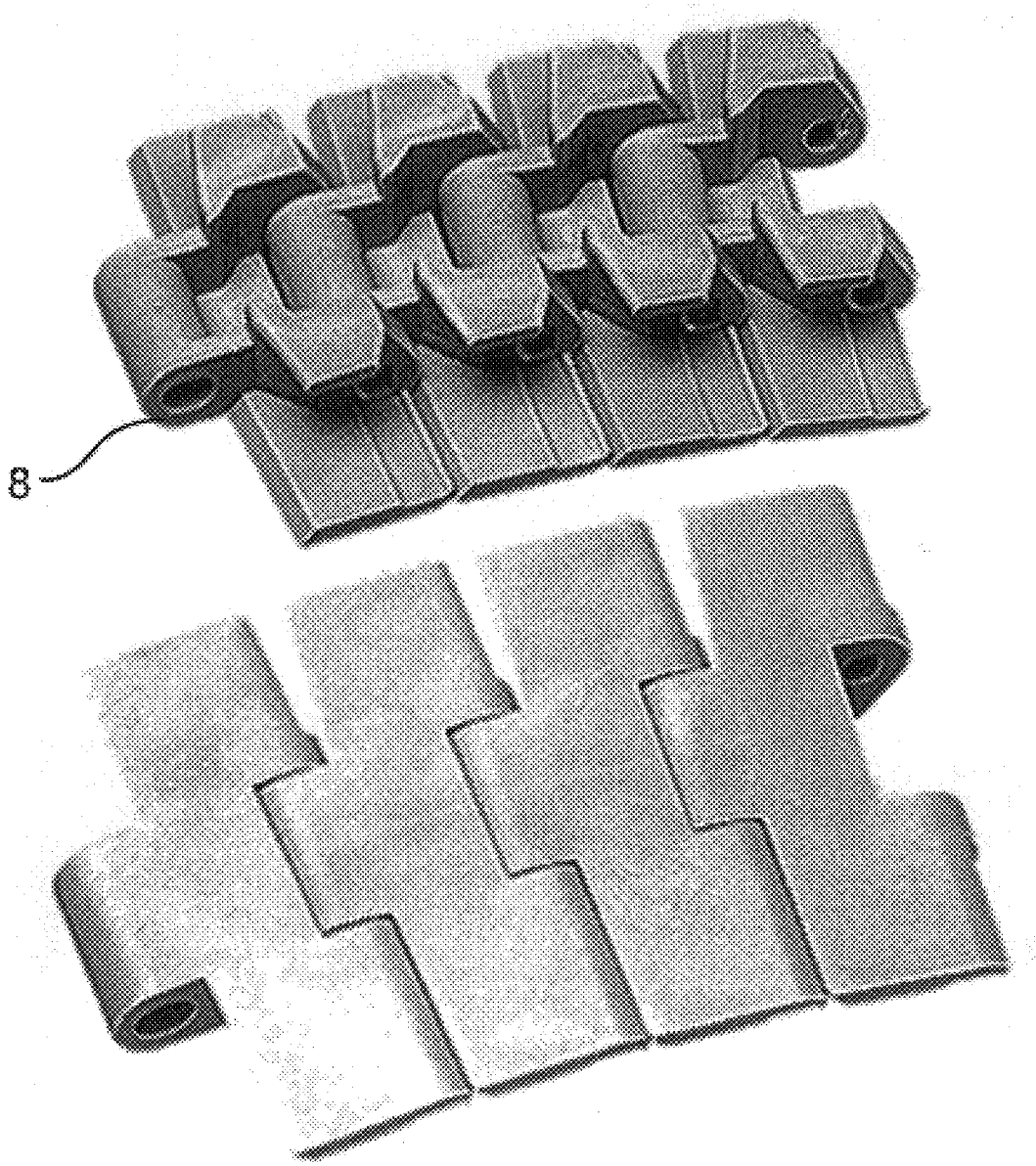
FIG. 3 shows another example of a conveyor component of the invention including a side flexing chain.
Figure 4:
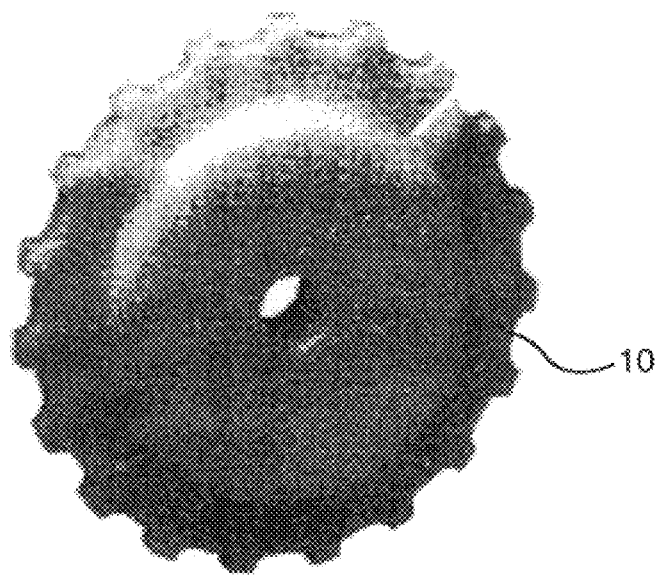
FIG. 4 shows a drive sprocket conveyor component of the invention.
Figure 5:
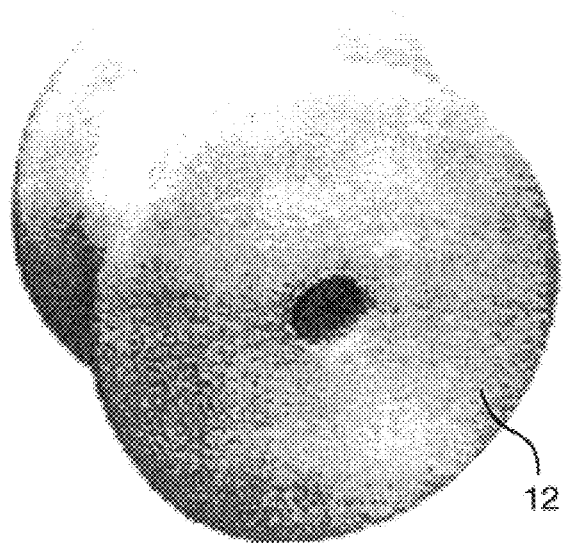
FIG. 5 shows an idler conveyor component of the invention.

Referring to the accompanying drawings, FIG. 1 shows a germicidally protected conveyor component of the invention in the form of a conveyor belt 2 comprising plate members 4 linked to each other. FIG. 2 shows an example of a germicidally protected running chain component 6 for a conveyor system. FIG. 3 shows an example of a germicidally protected side flexing chain component 8 in accordance with the present invention. FIG. 4 shows a germicidally protected drive sprocket 10 for a chain to be used in a conveyor system. FIG. 5 shows a germicidally protected idler component 12 in accordance with the present invention.

EXAMPLES

The invention will not be further illustrated with reference to the following non-limiting examples. In each of the examples the "Polymeric material" may any suitable material used in the fabrication of conveyor components, and is typically selected from polypropylene, polyethylene, nylon, acetal and polyurethane.

Example 1

The following composition of the invention was prepared

| Ingredients | Parts by Weight |
|---|---|
| Polymeric material | 95.00 |
| 2 Acrylamide-2-Methyl propane Sulfonic acid | 0.50 |
| Germicide Zinc Omadine | 5.00 |
| Hydroxy ethyl methacrylate | 0.10 |
| Ammonium persulfate | 0.01 |

-continued

| Ingredients | Parts by Weight |
| --- | --- |
| 0.1% solution | |
| Silver nitrate | 0.01 |
| 0.1% solution | |

Example 2

The following composition of the invention was prepared

| Ingredients | Parts by Weight |
| --- | --- |
| Polymeric material | 95.00 |
| 2 Acrylamide-2-Methyl propane Sulfonic Acid | 0.60 |
| Germicide Cetyl Pyridinium chloride | 5.00 |
| Sodium Omadine | 0.10 |
| Hydroxy ethyl methacrylate | 0.10 |
| Ammonium persulfate 0.1% solution | 0.01 |
| Silver nitrate 0.1% solution | 0.01 |

Example 3

The following composition of the invention was prepared

| Ingredients | Parts by Weight |
| --- | --- |
| Polymeric Material | 95.00 |
| Hydroxy ethyl methacrylate | 0.20 |
| Germicide Barquat 4250 | 10.00 |
| 2 Acrylamido-2-Methyl Propane Sulfonic Acid | 0.20 |
| Ammonium persulfate 10% solution | 0.10 |
| Ferrous ammonium sulfate | 0.40 |

Example 4

The following comparative tests have been carried out using four test specimens based on Example 1 (delrin) containing a germicide strength of (a) 0.5% by weight, (b) 1.0% by weight, (c) 3.0% by weight and (d) 5.0% by weight, together with a control specimen (delrin) containing no germicide.

Experimental

1. Organisms

Pure cultures and 7 bacteria and 1 fungus were ordered from the ATCC (American Type Culture Collection). The bacteria were: *Clostridium sporogenes, Escherichia coli, Klebsiella pneumoniae, Listeria monocytogenes, Salmonella choleraesius, Staphylococcus aureus* and *Streptococcus sanguis*. These organisms can cause health problems in humans. The particular varieties chosen for these tests have a history of being used in test protocols.

The fungus chosen was *Aspergillus flavus*, a source of aflatoxins. All organisms were cultured on appropriate agar media according to standard lab procedures.

Test #1. In this test, 1.0 ml of a broth solution of each organism was added to separate petri plates. Liquid agar media was added to the plates, swirled to mix thoroughly and allowed to harden. Within an hour, test samples of the test materials were surfaced, sterilized with 70% (by weight) of ETOH, dried and placed on the agar surface. Only one sample was placed per plate. All plates of bacteria were incubated at 37° C. for 24 hours. Method checks were included to test asepsis of the media, the distilled water, the hypodermic needles and all other equipment used. Other controls were included to insure the viability of the inoculum.

The fungus tests were similar, but different media were used and a lower incubation temperature (30° C.).

After incubation, plates were examined under 20X magnification. The evidence of the effectiveness of the test items was a clear zone in the agar media at the location of the test item.

The average distance from the edge of the test item to edge of the clear zone in the agar was measured with an ocular micrometer of the microscope. The size of the clear zones gives a measure of relative effectiveness of the several test concentrations against the various organisms. Each value in the following table for the size of the cleared zone is the average of 3 readings.

Results of Text #1:

| Conc. in test item | E. Coli | Lister. | Salmon. | Klebs. | Clostr. | Strept. | Staph. | Asperg. |
| --- | --- | --- | --- | --- | --- | --- | --- | --- |
| 0% | 0 | 0 | 0 | 0 | 0 | 0.6 | 0 | 0 |
| 0.5% | 0 | 0.9 | 1.7 | 2.3 | 0 | 1.2 | 1.1 | 0 |
| 1.0% | 0.1 | 1.6 | 3.1 | 3.0 | 0 | 0.5 | 1.0 | 0.5 |
| 3.0% | 2.1 | 5.1 | 3.3 | 1.8 | 2.5 | 2.7 | 3.8 | 1.0 |
| 5.0% | 3.7 | 4.4 | 4.8 | 6.0 | 5.4 | 4.7 | 4.9 | 2.0 |

Some of the irregularities in the data are due to uneven contact between the test item and the agar surface.

While there were obvious zones of bacterial inhibition in the test plates, some bacterial colonies were present in the clear zones in the agar media. The agar media was examined below the test item using 50X magnification.

The following statements summarize this data.

a. Clostridium: 30–50% of colonies survived and grew under all treated test items (0.5%–5.0%).

b. *E. coli*: Bacterial growth was entirely inhibited under all test treatments (0.5%–5.0%).

c. Klebsiella: Bacterial growth entirely inhibited for treatments 1.0%, 3.0% and 5.0%. The 5.0% treatment resulted in 50% growth of colonies showing poor growth.

d. Listeria: The 0.5% treatment has 30% colonies showing poor growth. The 1.0% had 5% colonies having poor growth. The 3.0% treatment had 1% of colonies, all with poor growth. The 5.0% treatment had no colonies growing.

e. Salmonella: The 0.5% and 1.0% treatments has 25% colony growth under the test items. The 3.0% and 5.0% had no bacterial growth under the test items.

f. Staphylococcus: The 0.5% treatment allowed 10% colony growth below the test item. The 1.0% treatment allowed 5% of colonies to grow. The 3.0% and 5.0% allowed no bacterial growth below the test items.

g. Streptococcus: The 0.5% and 1.0% allowed 50% colony growth below the test items. The 3.0% and 5.0% allowed no bacterial growth below the test items.

h. *Aspergillus flavus*: At the low concentrations (0.5%) the fungus grew and sporulated on the surface of the agar media. Slight sporulation occurred on the test items. At 1.0% and 3.0% concentration, the fungus grew and sporulated on the agar surface, but not on the surface of the test items. At 5.0%, the fungus grew poorly on the agar surface, with total inhibition on the polymer test items.

For the control test items, bacterial colonies of all 7 species grew below the test items in the agar media, that is, there was no inhibition of bacteria by the "control" test items. * Compared to the number of colonies in the part of the petri dish unaffected by the bacterial inhibitor.

It can seen from the results that an effective germicidal (antibacterial) agent has been incorporated into the test materials. The higher the concentration of anti-bacterial substance in the test materials, the greater its effectiveness and the greater the distance at which it inhibits bacteria. There is no evidence of migration of the germicidal agent out of the test sample.

The anti-bacterial material was effective against all the bacterial species tests but less so for Clostridium than the other bacterial species. However, Clostridium requires an anaerobic environment to survive and multiply—an unlikely condition in raw meat processing.

The 3.0% and 5.0% concentration of germicidal agent in the test materials is effective to inhibit all the test bacteria except Clostridium. The lower concentrations of antibacterial material, namely 0.5% and 1.0% were only partially effective in inhibiting these 7 bacterial species.

As with the bacterial species, the fungus *Aspergillus flavus*, was largely inhibited at the 3.0% and 5.0% concentrations.

While the invention has been described in what is considered to be the most practical and preferred embodiments, it is to be understood that the invention is not to be limited to the disclosed embodiments, and is intended to cover various modifications and equivalent arrangements included within the spirit and scope of the appended claims.

What is claimed is:

1. A process for fabricating a conveyor component having germicidal properties, which comprises the step of molding a blend of a polymeric material and a composition comprising a polymerizable monomer and a germicidal agent to form a conveyor component having germicidal properties comprising a solid unitary polymeric material and a polymerized salt of a polymerizable monomer and a germicidal agent grafted to said polymeric material and distributed uniformly throughout said polymeric material.

2. A process according to claim 1 wherein said molding is carried out by subjecting said blend to injection molding, extrusion molding or compression molding.

3. A process according to claim 1 wherein said composition comprising said polymerizable monomer and said germicidal agent is prepared by admixing said germicidal agent and said polymerizable monomer in the presence of a catalyst, graft initiator and a solvent.

4. A process according to claim 1 wherein said polymerizable monomer is an anionic polymerizable monomer and said germicidal agent is a cationic germicidal agent.

5. A process according to claim 1 wherein said polymeric material is selected from the group consisting of polypropylene, polyethylene, nylon, acetal and polyurethane.

* * * * *